United States Patent [19]

Wang

[11] Patent Number: 5,053,518

[45] Date of Patent: * Oct. 1, 1991

[54] HYDROXY-SUBSTITUTED CYCLIC-1,6-DIAZA[4.4]SPIRODILACTAMS

[75] Inventor: Pen-Chung Wang, Houston, Tex.

[73] Assignee: Shell Oil Company, Houston, Tex.

[*] Notice: The portion of the term of this patent subsequent to Jul. 3, 2007 has been disclaimed.

[21] Appl. No.: 524,412

[22] Filed: May 16, 1990

Related U.S. Application Data

[63] Continuation-in-part of Ser. No. 245,618, Sep. 16, 1988, Pat. No. 4,939,251, which is a continuation-in-part of Ser. No. 172,000, Mar. 23, 1988, abandoned, and a continuation-in-part of Ser. No. 172,052, Mar. 23, 1988, abandoned.

[51] Int. Cl.$^5$ ............................................ C07D 515/10
[52] U.S. Cl. .................................................... 548/410
[58] Field of Search ........................................ 548/410

[56] References Cited

U.S. PATENT DOCUMENTS

| | | | |
|---|---|---|---|
| 1,999,181 | 4/1935 | Conover et al. | 260/64 |
| 2,817,646 | 12/1957 | Payne | 260/78.3 |
| 4,064,086 | 12/1977 | Cowsar et al. | 260/29.2 R |
| 4,584,364 | 4/1986 | Lubowitz et al. | 528/128 |
| 4,701,566 | 10/1987 | Faler et al. | 568/719 |
| 4,939,251 | 7/1990 | Wang | 548/410 |

FOREIGN PATENT DOCUMENTS 224981 2/1982 Czechoslovakia ............... 549/265

OTHER PUBLICATIONS

Parzia et al., *Synthetic Communications*, vol. 13(3) 243–254 (1983).
Cava et al., *Journal American Chem. Society*, 77, 6022 (1955).
Wagner et al, "Synthetic Organic Chemistry," 1963, pp. 567–569.
Cava et al., *J. Am. Chem. Soc. Chem. Soc.*, 79, pp. 1706–1709 (1956).
Gourmelon et al., *Bull. Soc. Chem. Fr.*, 4032 (1971).

*Primary Examiner*—Robert T. Bond

[57] ABSTRACT

Novel cyclic 1,6-diazaspiro [4.4] lactams are produced by reaction of at least one hydroxy-containing primary amino compound with a 4-ketocyclicdiacid compound or a cyclic-1,6-dioxaspiro[4.4] lactone.

9 Claims, No Drawings

HYDROXY-SUBSTITUTED CYCLIC-1,6-DIAZA[4.4]SPIRODILACTAMS

CROSS-REFERENCE TO RELATED APPLICATION

This application is a continuation-in-part of Ser. No. 245,618, filed Sep. 16, 1988, now U.S. Pat. No. 4,939,251, which is a continuation-in-part of both Ser. Nos. 172,000 and 172,052, both now abandoned filed Mar. 23, 1988.

FIELD OF THE INVENTION

This invention relates to certain novel hydroxy-substituted cyclic-1,6-spirodilactams and to methods for their production. More particularly, it relates to [4,4] spirodilactams having nitrogen atoms in the 1-and 6-positions of the spiro ring system. Such spirodilactams are produced by reaction of at least one hydroxy-containing amino compound and a cyclic-spirodilactam precursor.

BACKGROUND OF THE INVENTION

A class of compounds having a polycyclic structure is the class of cyclic-spirodilactones represented by 3,4-(3,5-dimethoxybenzo)--8,9-benzo-1,6-dioxaspiro[4,4]nonane-2,7-dione. This spirodilactone is known, being prepared, for example, by Gourmelon et al., *Bull. Soc. Chem.*, 4032 (1971). It is generally considered characteristic of the spirodilactone ring system that reaction with active hydrogen compounds tends to produce ring-opened derivatives, as exemplified by the above Pariza et al., *Synthetic Communications*, Vol. 13 (3). pp. 243-254 (1983). publication and by Cowsar, U.S. Pat. No. 4,064,086. It would be of advantage to provide a process for converting the cyclic-spirodilactone ring system into novel functional derivatives while maintaining the spiro ring system.

SUMMARY OF THE INVENTION

This invention relates to novel hydroxy-substituted spirodilactam products and to methods for the production thereof. More particularly, the invention relates to novel [4.4] spirodilactams having one or more additional fused ring moieties within the spiro ring system, which fused ring moieties are additionally inertly substituted. Such spirodilactams are produced by reaction of at least one hydroxy-containing primary amino compound with a cyclic spirodilactam precursor selected from 4-ketocyclic dicarboxylic acid compounds or cyclic spirodilactones of corresponding ring structure.

DESCRIPTION OF THE INVENTION

The hydroxy-substituted cyclic-1,6-spirodilactams of the invention are produced by reaction of at least one hydroxy-containing primary amino compound, i.e., an organic compound having within the molecule a primary amino group (a —NH$_2$ group) and a hydroxyl group (a —OH group), with a spirodilactam precursor.

Such spirodilactam precursor compounds are also known compounds or are produced by known methods including the method described by Conover et al., U.S. Pat. No. 1,999,181, Cava et al., *J. Am. Chem. Soc.*, 77, 6022(1955), or Gourmelon et al., *Bull Soc. Chem.* 4032 (1971). Such methods include (1) in Conover et al., the decarboxylation of dicarboxylic acid anydrides in the presence of known decarboxylation catalysts, (2) in Cava et al., the chromic acid oxidation of cyclic (aryl) substituted dicyclic (diarylene) compounds, and (3) in Gourmelon et al., the Friedel Crafts condensation of cyclic (aryl) acid with cyclic (aryl) dicarboxylic anhydride. Other methods include Cava et al., *J. Am. Chem. Soc.*, 79, 1706 (1957) in which a fused ring-cyclobutene dibromide is treated with potassium hydroxide followed by oxidation with chromic acid in acetic acid, and Sikes et al., *Meeting Am. Chem. Soc.*, April 1988, p. 614, in which a cyclic magnesium bromide having an o-tolyl group is reacted with an excess of a dicarboxylic acid anhydride in benzene-ether solution followed by oxidation with chromium (VI) oxide in glacial acetic acid. Using these methods, spirodilactones in which —Z—Q$_m$ and —Z—Q$_n$ form fused ring derivatives substituted at the 3-, 3,5-, 3,4,5- or 3,4,5- and 6-positions can be prepared.

In one embodiment of the invention, the spirodilactam precursor is a ketodicyclic dicarboxylic acid compound having two carbon atoms between the center carbon of the keto group and each carboxy function. A variety of such ketodiacid compounds having a variety of substituents in addition to the oxo moiety and the carboxy groups, the preferred 4-oxoheptanedioic acid compounds have up to 30 carbon atoms inclusive and are represented by the formula Ia

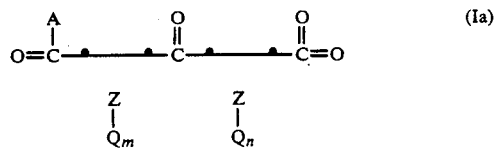

wherein A independently is hydroxy, alkoxy, preferably lower alkoxy of up to 4 carbon atoms, or halo, preferably the middle halogens chloro or bromo; and each Z together with the two carbon atoms to which it is attached independently is a saturated or unsaturated ring system of from 1 to 2 rings each having 5 to 6 ring atoms, up to two of which are heteroatoms selected from nitrogen, oxygen or sulfur heteroatoms with the remainder of the ring atoms being carbon atoms, two of which ring carbon atoms connect the central carbon atom, in this case the oxo carbon atom, with the carbon atom of a carboxy function. For example, the ring system is cycloaliphatic, aromatic or heterocyclic and is hydrocarbon containing only atoms of carbon besides any heteroatoms and at least one of Z is additionally inertly ringsubstituted by Q, wherein each Q is halogen. haloalkyl, alkyl, alkoxy, alkythio, tertiary-amino, tertiary-aminoalkyl, in which each alkyl group has up to 10 carbon atoms, preferably 4 carbon atoms, or aryloxy of up to 10 carbon atoms and 1 to 2 rings, with the proviso that at least one of m or n is not a zero such that one or more atoms of Z is substituted by other than a hydrogen atom, and each m and n independently is integers of 0 to 6, preferably 0 or 2. Illustrative of these cyclic ketodiacids are di-(2-carboxy(3,4,5-tribromo-phenyl)) ketone, di(2-carbethoxy(3,4,5,6-tetramethylphenyl)) ketone, di(2-carboxy(3,6-di(methylthio)cyclohexyl)) ketone, di(2-carboxy(3,5-di-methylpyridyl)) ketone, di(3-carbethoxy-2-(2-chloromorpholino)) ketone and di(3-carbomethoxy-2-(5-tert-aminonaphthyl)) ketone. The preferred cyclic ketodiacid compounds of this formula I are those wherein Z" is a ring system of from 5 to 6 atoms, inclusive, and up to one nitrogen and/or oxygen heteroatom.

In yet another embodiment of the spirodilactam precursor, the ketodiacid incorporates one fused cyclic moiety with the remainder of the Z moieties being >C(Z')$_2$, i.e., the compounds are of the formula Ib

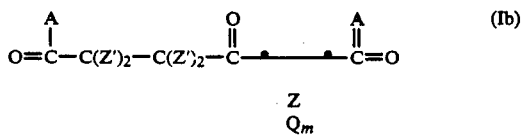

wherein A, Z, m and Q have the previously stated meanings and each Z' independently is hydrogen, alkyl of up to 4 carbon atoms, halogen or aryl of up to 10 carbon atoms, e.g., methyl, chloro, fluoro, phenyl or the like. Such ketodiacids of one cyclic moiety are illustrated by 3-(2-carboxy-(3,5-di(methoxy))benzoyl)propionic acid, 3-(2-carbomethoxy-4-chloro-2-pyridyloyl)-2-ethylpropionic acid, ethyl 3-(2-carbethoxy4-phenoxybenzoyl)propionate, 3-(2-carboxy-4-methylbenzoyl-butyrl) chloride and the like. The ketodiacids of the above formula IIIc are known compounds or are produced by known methods. For example, 2-carboxymethyl(4-methylbenz)aldehyde reacts with methyl acrylate according to the general teachings of U.S. Pat. No. 4,800,231, to produce methyl 3-(2-carbomethoxy(4-methylbenzoyl))propionate.

One class of such [4,4] spirodilactones is represented by the formula II a

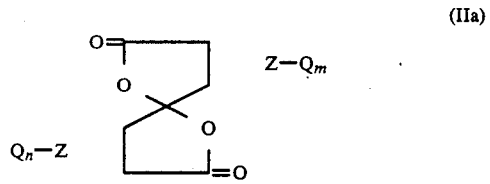

wherein Z and Q have the previously stated meaning with the understanding that two adjacent ring carbon atoms form a connecting group between a carbonyl carbon atom and the center carbon atom, in this case the spiro carbon atom, i.e., the carbon atom common to the two spiro rings.

In another embodiment, the spirodilactone-spirolactam precursors have the formula IIb

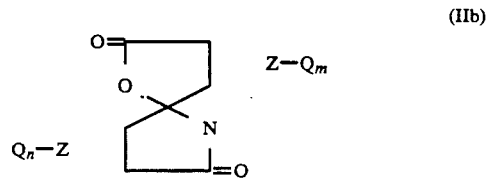

wherein Z, m, n and Q have the previously stated meaning. Typical compounds of this formula are 3,4,8,9-di(3,5-dimethoxybenzo)-1,6-dioxaspiro[4,4]-nonane-2,7-dione, 3,4-(3,4,5-tri(nitro)cyclopentano)-8,9-benzo-1,6-dioxaspiro[4,4]nonane-2,7-dione, 3,4,8,9-di(4-methylthiobenzo)-1,6-dioxaspiro[4,4]-nonane-2,7-dione, 3,4-(3,5-di(tertiary-aminomethylbenzo)-8,9-benzo-1,6-dioxaspiro[4,4]nonane-2,7-dione, 3,4,8,9-(di-(4-chloromethyl)-benzo)-1,6-dioxaspiro[4.4]nonane-2,7-dione, 3,4,8,9-di(3-phenylmorpholino)-1,6-dioxaspiro[4.4]nonane-2,7-dione, 3,4,8,9-di(3-chloropyrido)-1,6-dioxaspiro[4.4]nonane-2.7-dione, 3,4-(phenoxybenzo)-8,9-benzo-1.6-dioxaspiro[4.4]-nonane-2,7-dione and the like. These compounds of formula II are known compounds or are produced by known methods, for example, the processes described by Cava et al., *J. Am. Chem. Soc.*, 79, pp. 1706–1709 (1959) U.S. Pat. No. 1,999,181. Gourmelon et al., *Bull, Soc. Chem* . 4032(1971).

In another embodiment of the spirodilactone spirodilactam precursor, a cyclic moiety is fused to one spiro ring and the other spiro ring is free from fused ring substituents. Such spirodilactones are represented by the formula III

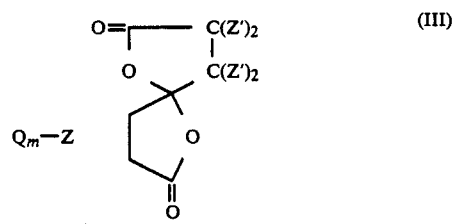

wherein Z, m, and Q have the previously stated meanings. Such spirodilactones are illustrated by 3-methyl-8,9-(3,5-di(methoxy)benzo)-1,6-dioxaspiro[4.4]nonane-2,7-dione, 3,4-(4-methylbenzo)-1,6-dioxaspiro[4.4]nonane-2,7-dione, and 3,3,4,4-tetramethyl-8,9-(2-chloromorpholino-1,6-diazaspiro[4.4]nonane-2,7-dione and the like. The spirodilactones of the above formula III are produced by known methods, for example, the dehydration of the corresponding ketodiacid. By way of illustration, 3,4-(3.5-di(methoxy)benzo)-1,6-dioxaspiro[4.4]nonane-2,7-dione, is produced by condensation of succinic acid anhydride with 3,5-dimethoxy benzoic acid methyl ester.

An especially preferred spirodilactone spirodilactam precursor is 3,4-(3,5-dimethoxybenzo)-8,9-benzo-1,6-dioxaspiro[4.4]nonane-2,7-dione.

Suitable spirodilactam precursors and their preparation are also described in U.S. Pat. Nos. 4,847,388 and 4,885,351, the disclosures of which are incorporated herein by reference.

In the process of the invention, the spirodilactam precursor is reacted with at least one hydroxy-containing primary amino compound to produce a [4.4] spirodilactam having at least one nitrogen atom within the spiro ring in a position adjacent to the spiro carbon atom, i.e.. the carbon atom common to the two rings, and having a hydroxy-containing substituent attached to each nitrogen atom. The process is adaptable to the production of a variety of spirodilactam products, as is discussed below, depending on the molar ratio of the reactants and the nature of the primary amino compound(s) employed. In one modification, the spirodilactam precursor is reacted with a molar excess, say a two-fold excess, of one or two. preferably one, hydroxy-containing primary amino compounds. Reaction serves to produce a [4.4] spirodilactam having nitrogen atoms in the 1- and the 6-ring positions with the portion of the hydroxy-containing primary amino compound. i.e., the portion remaining when the amino group is excluded, as a substituent on each nitrogen atom. In an alternate modification, a limited molar amount of hydroxy-containing primary amino compound, e.g., no more than one mole per mole of spirodilactam precursor, reacts with the spirolactam precursor to produce a spirolactam-lactone having the oxygen and nitrogen atoms in the 1- and 6-positions of the spiro ring system with the remainder of the hydroxy-containing primary amino compound as a substituent on the nitrogen atom and then the spirolactam-lactone is further reacted with the same or a different hydroxy-containing primary amino compound.

The hydroxy-containing primary amino compound(s) with which the spirolactam precursor reacts as well as any hydroxy-free primary amino compound are of a variety of chemical structures. The precise nature of the group that links the hydroxy group and the amino group, as well as the group to which the primary amino group is attached in the hydroxy-free primary amino compound, is not critical provided that at least three carbon atoms separate the amino group from any hydroxyl group and the group does not provide sufficient steric hindrance to preclude reaction of the amino group with the spirolactam precursor. The linking group is therefore suitably (cyclo)aliphatic or aromatic (suitably (cyclo) alkylene, or arylene) or mixed (cyclo)aliphatic and aromatic and is hydrocarbyl or is substitutedhydrocarbyl with any atoms other than carbon and hydrogen being present as inert substituents such as middle halo or as divalent portions of the linking groups. In one embodiment the primary amino compound is what is commonly termed a "large molecule" and is an oligomer, prepolymer or polymer which is functionalized to include a primary amino group and optionally a hydroxyl group. A preferred class of primary amino compounds, however, has up to 30 carbon atoms and up to 4 aromatic rings, inclusive, and is represented by the formula IV $$H_2N-R-X(-R)_r-OH \quad (.HY)_m \qquad (IV)$$

wherein each R independently is a (cyclo)aliphatic or aromatic group of up to 10 carbon atoms, inclusive; each m and r is independently 0 or 1; X is a direct valence bond, an alkylene group of up to 8 carbon atoms inclusive, oxy, thio, sulfonyl, carbonyl, dioxyphenylene, e.g.,

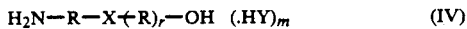

2,2-bis(oxyphenyl)propane, e.g.,

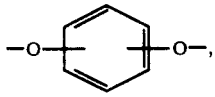

or dioxydiphenylene, e.g.,

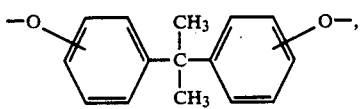

and HY is an acid which forms a salt with the amine, including both inorganic and organic acids which do not interfere with the reaction, such as hydrohalogenic acids, for example, hydrochloric and hydrobromic, sulfur acids, for example surfuric or sulfonic, phosphorus acids, for example phosphoric or phosphonic; and carboxylic acids, for example oxalic and the like. Preferably, Y is halogen, e.g., fluorine, chlorine, bromine or iodine and especially chlorine or bromine.

Illustrative of the primary amino compounds of the above formula IV are p-aminophenol, 6-aminohexanol, 1-amino-5-hydroxynaphthalene, 4-aminophenyl 3-hydroxyphenyl ether. 2-(3-hydroxyphenylthio)ethylamine, 4-amino-1'-hydroxybiphenyl, 2-hydroxypropyl 4-aminophenyl ketone, m-aminophenol, 1-(4-hydroxyphenyloxy)-3-(3-aminophenyloxy)benzene. 2-(3-hydroxyphenyloxyphenyl)-2-(2-aminophenoloxyphenyl)propane, 5-(4-aminophenyl)-1-pentanol, (4-aminophenyl)(3-hydroxyphenyl)methane, 2-(4-aminophenyl)-2-(4-hydroxyphenyl)propane, 4-amino-3-chlorophenol, 4-amino-o-cresol, 4-(2-aminoethyl)-phenol and 4-aminocyclohexanol.

The compounds wherein all R groups present in the molecule are aromatic are preferred over the primary amino compounds wherein an aliphatic R group is present, especially those primary amino compounds which are otherwise hydrocarbyl and wherein r is 0. The aminophenols are a preferred class of hydroxy-containing primary amino compounds, particularly p-aminophenol.

The spirolactam precursor is contacted with at least one hydroxy-containing primary amino compound to produce a [4.4] spirodilactam, the nature of which will depend upon the choice of spirodilactam precursor and the ratio of reactants which is employed. When the ratio of reactants is such that the spirolactam precursor is present in a molar quantity of about equal to or greater than the molar quantity of hydroxy-containing primary amino compound, the predominant product is a spirolactam-lactone wherein the amino moiety of the hydroxy-containing primary amino compound has been incorporated into the spiro ring system with the amino nitrogen being located in the ring system in a position adjacent to the spiro carbon atom, the remainder of the hydroxy-containing primary amino compound being present as a substituent on the ring nitrogen atom and a lactone group being present with the non-carbonyl lactone oxygen also present in a ring position adjacent to the spiro carbon atom. Ths is then reacted with addtional hydroxy-containing primary amine compound to obtain the spirodilactam.

Another embodiment of the process of the invention leads to the production of a spirodilactam which, in terms of the spirolactam precursor and the primary amino compounds described above, is represented by the formula Va or Vb

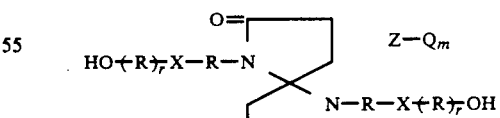

(Va)

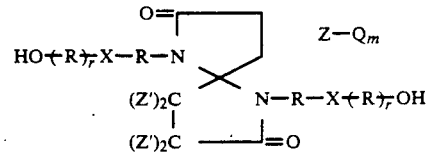

(Vb)

wherein R, r, m, n. X and Z, Z' and Q have the previously stated meanings. Such a spirodilactam is produced by several alternative processes, depending largely upon the particular spirodilactam product desired. In one embodiment, a spirodilactam having a hydroxy-containing substituent on each of the spiro ring nitrogen atoms, e.g., a compound of the above formula Va or Vb, is produced from hydroxy-substituted primary amino compound and spirolactam precursor in one reaction step. In this embodiment, the hydroxy-substituted primary amino compound is employed in a molar quantity in excess of the hydroxy-substituted primary amino compound. To obtain a spirodilactam as the predominant product, the molar quantity of hydroxycontaining primary amino compounds is preferably at least about twice the molar quantity of spirolactam precursor. The quantity of hydroxy-containing primary amino compound may comprise a single hydroxy-containing primary amino compound, in which case a single hydroxy-containing primary amino product of the above formula Va or Vb will be obtained. Alternatively, a mixture of hydroxy-containing primary amino compounds, e.g., two such amino compounds, may be utilized and a spirodilactam containing two different hydroxy-containing spiro ring nitrogen substituents will be obtained as well as lesser amounts of each spirodilactam having the same hydroxy-containing substituent present as derived from each of the hydroxy-containing primary amino compounds employed as reactant.

In order to obtain a spirodilactam in which the hydroxy-containing spiro ring nitrogen substituents are different, a somewhat different twostep process is preferred. Initially, a hydroxy-substituted primary amino compound in limited molar quantity is reacted with the spirolactam precursor to obtain a spirolactam-lactone product of the above formula Va or Vb. The spirolactam-lactone, with or without isolation or purification, is then reacted with a second hydroxy-containing primary amino compound to produce a spirodilactam of formula Va or Vb wherein the hydroxy-containing substituents on the spiro ring nitrogen atoms are different.

Regardless of the particular reaction of primary amino compound with spirodilactam precursor according to the process of the invention, the reaction preferably takes place in a liquid phase in the presence of an inert reaction diluent which is liquid at reaction temperature and pressure. Preferred reaction diluents are liquid inert polar reaction diluents in which the primary amino compound reactant and the spirolactam precursor or spirolactam-lactone are soluble. Suitable diluents include dialkyl ketones such as methyl ethyl ketone, methyl isobutyl ketone and di-i-propyl ketone; esters such as butyl acetate and methyl 2-ethylhexanoate; ethers including acylic ethers such as diethyleneglycol diethyl ether and tetraethyleneglycol dimethyl ether as well as cyclic ethers such as dioxane and tetrahydrofuran; sulfur-containing diluents such as sulfolane and dimethyl sulfoxide; and N-alkylamides such as N,N-dimethylacetamide, N,N-dimethylformamide and N-methyl-2-pyrrolidone. The N-alkylamides are a preferred class of reaction diluents, particularly N-methyl-2-pyrrolidone.

The spirodilactam precursor and the primary amino compound are contacted under reaction conditions in solution in the reaction diluent by conventional methods such as stirring, shaking or refluxing. Suitable reaction temperatures are from about 80° C. to about 250° C., preferably from about 100° C. to about 200° C., depending in part upon the particular reaction diluent employed. Suitable reaction pressures are those sufficient to maintain the reaction mixture in a liquid phase. Typically such pressures are up to about 20 atmospheres but more often are from about 0.8 atmospheres to about 10 atmospheres.

The ratio of the reactants to be employed depends greatly upon the type of product which is desired. To produce a spirodilactam of formula Va or Vb by reaction of a hydroxy-containing primary amino compound and a spirolactam precursor, a molar ratio of amino compound to spirolactam precursor from about 1.5:1 to about 8:1 is satisfactory, although higher ratios are also satisfactory. Molar ratios of amino compound to spirolactam precursor from about 1.8:1 to about 3:1 are preferred.

Subsequent to reaction, the spirodilactam product is recovered, if desired, by conventional methods such as precipitation, selective extraction or distillation. If, however, the initial spirolactam product is a spirolactam-lactone product to be employed in a subsequent conversion to a spirodilactam, it is not generally necessary to separate the initial product and the reaction to produce spirodilactam is often conducted with isolating the spirolactam-lactone.

The hydroxy-substituted spirodilactams find utility as precursors of resin materials, substituents are particularly useful because of the structural feature of having a polycyclic center portion with hydroxyl groups on the outer portions of the molecule. By way of specific illustration, such spirodilactams are reacted with epichlorohydrin to produce corresponding di(glycidyloxy)-substituted spirodilactams which are cured with conventional epoxy curing agents to produce insoluble thermoset resins having good properties of strength and rigidity with a desirable glass transition temperature. The production of the diglycidyl derivatives of the hydroxy-substituted spirodilactams is described more fully and is claimed in U.S. Pat. No. 4,895,942, incorporated herein by reference.

The invention is further illustrated by the following Illustrative Embodiments which should not be construed as limiting.

Illustrative Embodiment I

A mixture of 13.75 g (0.044 mols) of 3,4-(3,5-dimethoxybenzo)--8,9-benzo-1,6-dioxaspiro[4.4]nonane-2,7-dione (prepared by the method of Gourmelon et al., *Bull. Soc. Chem.*, 4032 (1971)) and 9.61 g (0.088 mole) of p-aminophenol and 45 ml of 1-methyl-2-pyrrolidinone was placed in a 300 ml round-bottomed flask equipped with a mechanical stirrer and a condenser. The mixture was heated to 150°–160° C. with stirring and until the reaction was complete. After cooling, the solvent was removed under reduced pressure and methanol was added to precipitate the product. The precipitated product had a nuclear magnetic resonance spectra consistent with the structure of formula Vb for 1,6-di(4-hydroxyphenyl)-3,4-(3,5-di(methoxy)benzo)-8,9-benzo-1,6-diazaspiro-[4.4]nonane-2,7-dione.

What is claimed is:

1. A compound of the formula V

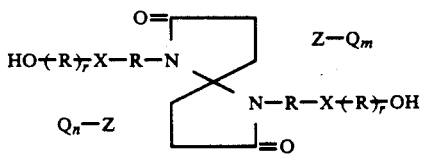
(Va)

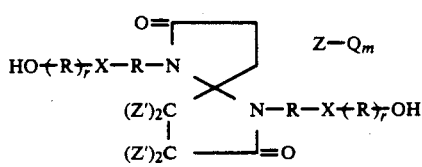
(Vb)

wherein Z is a saturated or unsaturated ring system of from 1 to 2 rings each having 5 to 6 ring atoms, up to two of which are heteroatoms selected from nitrogen, oxygen or sulfur with the remainder of the ring atoms being carbon atoms, two of which form a bridge between the carbon atom of a carboxy function and the center ring spiro carbon atom; R independently is (cyclo)aliphatic or aromatic of up to 10 carbon atoms, inclusive; r is 0 or 1; each m and n independently is an integer of 0 to 6; each Q is independently halogen, haloalkyl, alkyl, alkoxy, alkylthio, tertiary-amino, tertiary-aminoalkyl, in which each alkyl has up to 10 carbon atoms, or aryloxy of up to 10 carbon atoms and 1 to 2 rings, with the proviso that at least one of m and n is not zero; Z' is hydrogen, alkyl of up to 4 carbon atoms, halogen or aryl of up to 10 carbon atoms; and X is a direct valence bond, an alkylene group of up to 8 carbon atoms, inclusive, oxy, thio. sulfonyl, carbonyl. dioxyphenylene. 2,2-bis(oxyphenyl)propane or dioxydiphenylene.

2. The spirodilactam of claim 1 wherein each R is aromatic.

3. The spirodilactam of claim 2 wherein each R is a phenylene group.

4. The spirodilactam of claim 3 wherein each Z together with the two spiro ring carbon atoms to which it is attached form a benzene ring and m and n each independently is 0, 1 or 2.

5. The spirodilactam of claim 4 wherein each X is a direct bond.

6. The spirodilactam of claim 5 wherein each r is 0.

7. The compound of claim 6 wherein m is 2 and n is 0, 1 or 2.

8. The compound of claim 7 wherein Q is methoxy.

9. The compound of claim 8 of formula Va which is 1.6-di(4-hydroxyphenyl)-3,4-(3,5-(dimethoxybenzo)-8,9-benzo-1,6-diazaspiro[4.4]-nonane-2,7-dione.

* * * * *